United States Patent [19]

Cuillerdier et al.

[11] Patent Number: 5,510,090
[45] Date of Patent: Apr. 23, 1996

[54] PROCESS FOR THE SELECTIVE EXTRACTION (III) ACTINIDES BY MEANS OF AMIDES HAVING A NITROGENOUS HETEROCYCLIC SUBSTITUENT

[75] Inventors: Christine Cuillerdier, Paris; Claude Musikas, Bures, both of France

[73] Assignee: Commissariat A l'Energie Atomique, Paris, France

[21] Appl. No.: 94,046

[22] PCT Filed: Dec. 2, 1992

[86] PCT No.: PCT/FR92/01124

§ 371 Date: Jul. 27, 1993

§ 102(e) Date: Jul. 27, 1993

[87] PCT Pub. No.: WO93/11113

PCT Pub. Date: Jun. 5, 1993

[30] Foreign Application Priority Data

Dec. 5, 1991 [FR] France ............... 91 15086

[51] Int. Cl.⁶ ............... C01G 56/00; C01G 43/00; C01F 17/00
[52] U.S. Cl. ............... 423/9; 546/169; 546/323
[58] Field of Search ............... 546/323, 169; 423/9

[56] References Cited

U.S. PATENT DOCUMENTS

| | | | |
|---|---|---|---|
| 4,496,523 | 1/1985 | Bonnin | 423/8 |
| 4,572,802 | 2/1986 | Hubert et al. | 534/12 |
| 4,715,888 | 12/1987 | Marzolph et al. | 504/134 |
| 4,770,807 | 9/1988 | Musikas et al. | 252/184 |
| 4,923,686 | 5/1990 | Dalton | 423/38 |
| 4,938,871 | 7/1990 | Musikas et al. | 210/634 |

FOREIGN PATENT DOCUMENTS

| | | |
|---|---|---|
| 0043765 | 1/1982 | European Pat. Off. . |
| 0057797 | 8/1982 | European Pat. Off. . |
| 0070226 | 1/1983 | European Pat. Off. . |
| 0138002 | 4/1985 | European Pat. Off. . |
| 0210928 | 2/1987 | European Pat. Off. . |
| 567475 | 10/1975 | Switzerland . |

OTHER PUBLICATIONS

Chemical Abstracts, 1965–1971, Registry Handbook, Columbus, Ohio US: RN 30721–98–3, 2632–42–0, 22989–55–5; RN 6144–78–1, 7606–13–5, 17038–66–3; RN 10354–51–5.
Chemical Abstracts, 1973, Registry Handbook, Columbus, Ohio US: RN 42182–43–4, 42182–33–2, 41116–47–6.
Chemical Abstracts, 1981, Registry Handbook, Columbus, Ohio US: RN 77074–35–2, 77074–36–3.
Chemical Abstracts, 1983, Registry Handbook, Columbus, Ohio US: RN 84678–82–0, 86996–11–4.
Chemical Abstracts, 1984, Registry Handbook, Columbus, Ohio US: RN 90173–74–3, 89047–40–5, 89047–41–6, 88561–57–3.
Chemical Abstracts, 1986, Registry Handbook, Columbus, Ohio US: RN 105655–06–9.
Chemical Abstracts, 1987, Registry Handbook, Columbus, Ohio US: RN 107427–71–4, 107427–70–3.
Chemical Abstracts, 1990, Registry Handbook, Columbus, Ohio US: RN 126230–29–3, 126230–13–5, 130317–79–2, 127682–94–4.

*Primary Examiner*—C. Warren Ivy
*Assistant Examiner*—D. Margaret M. Mach
*Attorney, Agent, or Firm*—Pearne, Gordon, McCoy & Granger

[57] ABSTRACT

The invention relates to a process for the selective extraction of (III) actinides by means of amides having a nitrogenous heterocyclic substituent of formula:

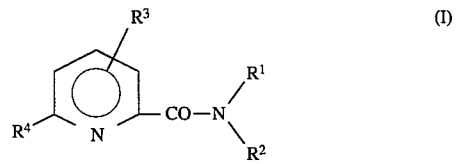

(I)

or

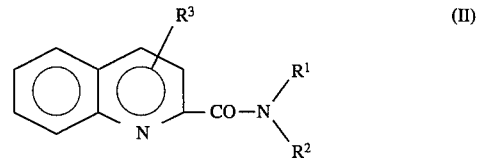

(II)

in which $R^1$ is an alkyl or alkoxy group or a hydrogen atom, $R^2$ and $R^3$, which can be the same or different, represent a hydrogen atom, an alkyl or an alkoxy group and $R^4$ is a hydrogen atom or a group of formula:

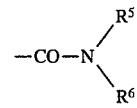

in which $R^5$ and $R^6$, which can be the same or different, represent a hydrogen atom or an alkyl or alkoxy group. This process makes it possible to separate (III) actinides from (III) lanthanides.

16 Claims, No Drawings

PROCESS FOR THE SELECTIVE EXTRACTION (III) ACTINIDES BY MEANS OF AMIDES HAVING A NITROGENOUS HETEROCYCLIC SUBSTITUENT

This application is a 371 of PCT/FR92/01124, filed 2 Dec. 1992. The present invention relates to a process for the selective extraction of (III) actinides by means of amides having a nitrogenous heterocyclic substituent more particularly usable for separating trivalent actinides from trivalent lanthanides.

In irradiated nuclear fuel reprocessing installations, during the initial extraction stages, normally uranium and plutonium are obtained, together with aqueous solutions of fission products containing relatively large quantities of trivalent ions from the lanthanide and actinide series. The aqueous effluents from such installations also contain the same ions.

In view of the very long half-life of actinide elements, it is very important to be able to separate all the (III) actinides from the (III) lanthanides, if it is wished to carry out an extensive reprocessing and eliminate the (VI), (IV) and (III) actinides from all the waste materials.

For the transmutation of the separated actinides, it is necessary to separate the lanthanides, which are poisons during the nuclear reactions used for the transmutation.

Up to now the trivalent actinides have been extracted from the aqueous solutions by using organic extractants and in particular propane-diamides, as described in FR-A-2 537 326 and FR-A-2 585 692. However, these extractants are not completely satisfactory, because they lack selectivity for the trivalent ions of series 4f and 5f, whose ionic radii are in the range 0.09 to 0.11 nm and they consequently simultaneously extract trivalent lanthanides. Thus, the ligands, whose interaction with the trivalent ions of series f is of the purely ionic type, do not selectively complex the trivalent lanthanides or actinides.

In order to carry out such a separation, up to now use has been made of other ligands, e.g. mixtures of ligands, such as the mixture of 2,4,6-tri-(2-pyridyl) 1,3,5-triazine and dinonyl naphthalene sulphonic acid described in FR-A-2 509 282 and the mixture of Di-2-ethyl hexyl dithiophosphoric acid and tributyl phosphate or trioctyl phosphine oxide described in EP-A-43 765.

Although these mixtures give good results, research has continued for finding other organic ligands which can be used alone for selectively extracting actinides or lanthanides. This research has led to the finding that amides with a nitrogenous heterocyclic substituent had this property and are suitable for selectively extracting trivalent actinides and for separating them from the trivalent lanthanides.

The present invention therefore relates to a process for the selective extraction of the trivalent actinides present in an aqueous solution, characterized in that it consists of extracting the trivalent actinides by an amide having a nitrogenous heterocyclic substituent of formula:

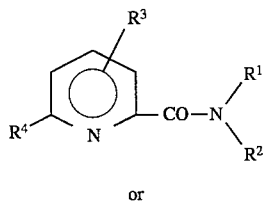

or

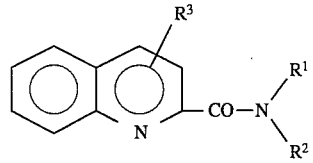

in which $R^1$, $R^2$ and $R^3$, which are the same or different, represent hydrogen atom or an alkyl or alkoxy group and $R^4$ represents a hydrogen atom or a group of formula:

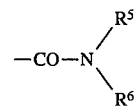

in which $R^5$ and $R^6$, which are the same or different, represent a hydrogen atom or an alkyl or alkoxy group.

In the above formulas, the alkyl and alkoxy groups which can be used can be straight or branched and generally have 1 to 24 carbon atoms.

The amides with a nitrogenous heterocyclic substituent according to the above formulas (I) and (II) are complex compounds with oxygen and nitrogen donor atoms.

In these molecules, nitrogen is a weaker donor than the oxygen of the conventional extractants and it can give rise to partly covalent bonds. As the covalency is higher with ions of the 5f series, this leads to a stronger complexing with respect to the actinides than the lanthanides, so that the said actinides can be selectively extracted from a mixture of trivalent lanthanides and actinides.

These amides are of interest, because they are completely incineratable organic molecules, so that it is easily possible to solve the problems of the processing of waste when said amides are used as the solvent in an active medium for actinide - lanthanide separation.

The amides having a nitrogenous heterocyclic substituent according to the invention can be prepared by conventional processes from the corresponding acid chlorides.

Thus, it is possible to prepare an amide having nitrogenous heterocyclic substituent of formula:

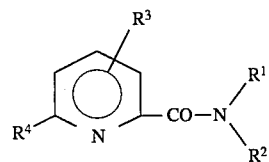

or

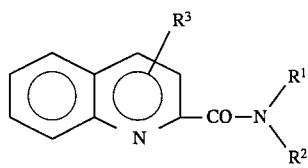

in which $R^1$, $R^2$ and $R^3$ have the meanings given hereinbefore and $R^4$ is a hydrogen atom, by reacting an acid chloride of formula:

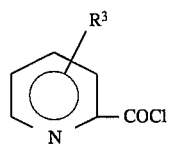

or

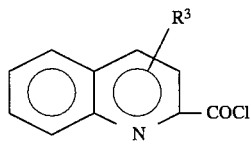 (IV)

in which $R^3$ has the meaning given hereinbefore with an amine of formula:

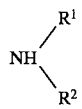 (V)

in which $R^1$ and $R^2$ have the meanings given hereinbefore.

In the case of the amide of formula (I) with $R^1$ representing a group of formula:

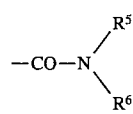

in which $R^5$ and $R^6$ have the meanings given hereinbefore, the diacid chloride of formula:

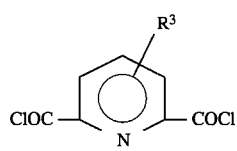 (VI)

(in which $R^3$ has the meaning given hereinbefore) is reacted with an amine or a mixture of amines in accordance with the formulas:

 (V)

and

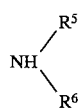 (VII)

in which $R^1$, $R^2$, $R^5$ and $R^6$ have the meanings given hereinbefore.

When using a mixture of amines, it is then necessary to separate the desired amide having a nitrogenous heterocyclic substituent, because the reaction leads to a mixture of amides. This separation can take place by conventional processes, e.g. by distillation under reduced pressure or column chromatography.

The acid chlorides of formula (III), (IV) and (VI) used as the starting product in these processes are commercial products or can be prepared by conventional processes.

According to the invention, the process for the selective extraction of the trivalent actinides present in an aqueous solution consists of complexing these trivalent actinides by an amide having a nitrogenous heterocyclic substituent of formula:

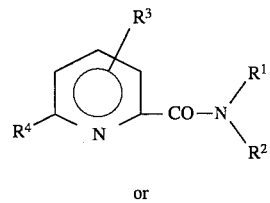 (I)

or

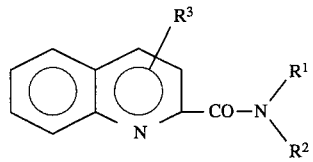 (II)

in which $R^1$, $R^2$ and $R^3$, which can be the same or different, represent a hydrogen atom, or an alkyl alkoxy group and $R^4$ represents a hydrogen atom or a group of formula:

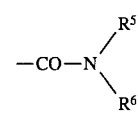

in which $R^5$ and $R^6$, which can be the same or different, represent a hydrogen atom, an alkyl group or an alkoxy group.

In general, it comprises the following stages:

a) contacting a nitric aqueous solution containing the trivalent actinides with an organic solution incorporating at least one amide having a nitrogenous heterocyclic substituent of formula:

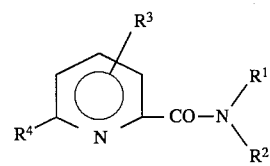 (I)

or

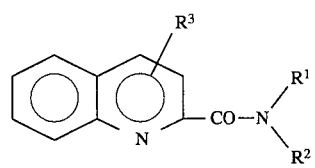 (II)

in which $R^1$ is a hydrogen atom, or an alkyl or alkoxy group, $R^2$ and $R^3$, which are the same or different, represent a hydrogen atom, or an alkyl or alkoxy group and $R^4$ represents a hydrogen atom or a group of formula:

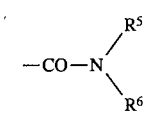

in which $R^5$ and $R^6$, which are the same or different, represent a hydrogen atom, or an alkyl or alkoxy group and b) separating the organic solvent which has extracted the actinides from the aqueous solution.

For said extraction, it is preferable to use an amide having a nitrogenous heterocyclic substituent in which $R^1$ represents an alkyl or alkoxy group and $R^2$ represents a hydrogen atom, because with such amides there is a better extraction of the trivalent actinides.

As examples of such amides, reference can be made to those according to formula (I) with $R^1$ representing an alkyl group and $R^2$, $R^3$ and $R^4$ representing a hydrogen atom.

For performing the extraction process according to the invention, the amide having the nitrogenous heretocyclic substituent is generally dissolved in an appropriate organic diluent. This diluent can e.g. be an aromatic diluent, an aliphatic diluent or an amide.

For example, it is possible to use as the diluent benzene and benzene derivatives, e.g. tert. butyl benzene, or an amide such as dibutyl formamide.

However, it is also possible to use amides having a nitrogenous heterocyclic substituent in the pure state without a diluent, but in this case it is sometimes necessary to work at a temperature above ambient temperature, when the product is solid at ambient temperature.

In order to favour the selective extraction of trivalent actinides $Ac^{3+}$, the starting nitric aqueous solution must have a not very high nitric acid concentration, which is preferably below 0.5 mole/l, in order to avoid the $Ac^{3+}/H^+$ competing with the amide of formula (I) or (II).

According to a preferred performance procedure for the process according to the invention suitable for the separation of the trivalent lanthanides and actinides present in a nitric aqueous solution, to said solution is added a nitrate or a thiocyanate in order to assist the (III) actinide/(III) lanthanide separation.

As examples of such thiocyanates, reference can be made to ammonium thiocyanate and the thiocyanates of alkali metals such as sodium or potassium. The added thiocyanate quantity is in particular dependent on the actinide quantities to be extracted. Generally, the thiocyanate concentration of the aqueous solution is 0.01 to 2 mole/l and preferably 0.025 to 2 mole/l.

When using a nitrate, it is e.g. possible to use lithium or sodium nitrate with concentrations between 1 and 10 mole/l.

The process of the invention can be performed in conventional extraction equipment such as mixer—settler groups, exchange columns, e.g. pulsed columns, centrifugal extractors, etc.

Working generally takes place at ambient pressure and temperature with volume ratios of the aqueous solution to the organic solvent between e.g. 0.1 and 10.

However, it is possible to work at temperatures above ambient temperature, e.g. when using as the organic solvent the pure amide of formula (I) or (II).

The actinides selectively extracted in the organic solvent can then be recovered with very good yields by reextraction in an aqueous phase constituted by a very highly diluted solution, which neither complexes, nor salts out, e.g. $10^{-3}M$ $HNO_3$.

Other features and advantages of the invention can be better gathered from reading the following examples given in a purely illustrative and non-limitative manner.

EXAMPLE 1: PREPARATION OF N-dodecyl-2-pyridine carboxamide (compound 1)

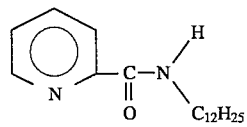

In this example, the starting product used is 2-picolinic acid of formula:

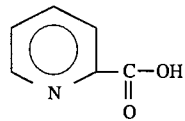

which is a commercial product.

This acid is mixed with a thionyl chloride excess and refluxed for 2 hours in the presence of a few drops of dimethyl formamide as the catalyst. This gives the acid chloride of formula:

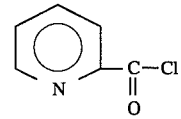

according to the reaction:

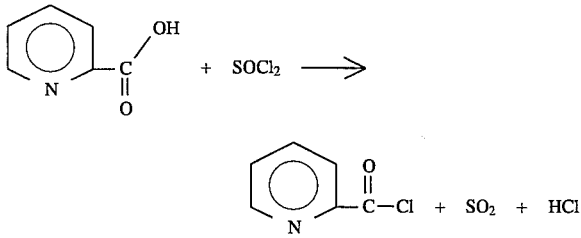

the excess of $SOCl_2$, which has not reacted, being eliminated by azeotropic distillation in the presence of benzene or by simple distillation—the other products of the reaction being volatile. The second stage consists of reacting said acid chloride with dodecyl amine $H_2N$—$C_{12}H_{25}$, which is a commercial product.

For this procedure use is made of the same preparation method as used for the monoamides described by G. Thiollet and C. Musikas in Solvent Extraction and Ion Exchange, 3-813, 1989, i.e. the amine diluted in chloroform is placed in a three-necked flask degassed by nitrogen. Triethyl amine $(C_2H_5)_3N$ is added for trapping the HCl and cooling takes place to 5° C.

The acid chloride diluted in chloroform is added dropwise, whilst maintaining the temperature at approximately 5° C. and stirring. The $CHCl_3$ is then boiled and allowed to reflux for 2 hours. After cooling, the excess triethylamine and triethylamine chloride are eliminated by washing with water. The amide is in this case a solid (m.p. 47° C.), which is washed and dried. The overall reaction is written as follows:

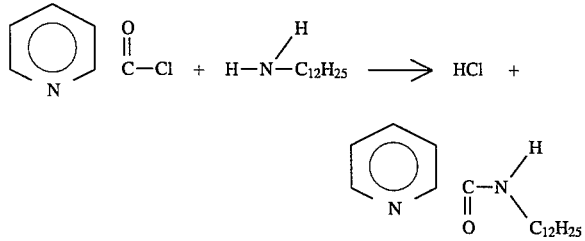

EXAMPLES 2 TO 4

These examples adopt the same operating procedure as in example 1 for comparing compounds 2, 3 and 4 of Table 1, but using the amines of Table 1 in place of lauryl amine. This gives the amides of Table 1.

EXAMPLE 5

In this example, determination takes place of the formation constants of complexes of trivalent ions constituted by lanthanides ($Nd^{3+}$ and $Er^{3+}$) and actinide ($Am^{3+}$), with the ligands according to the invention.

For the determination of these constants, use is made of an aqueous medium containing the ion to be complexed or a methanol—water medium when the ligand has a limited solubility in the aqueous phase. The formation constants of the complexes obtained with the following ligands: pyridine-2-carboxamide and compounds 2 and 3 of Table 1 are given in Table 2.

Table 2 shows that there is an important variation between the formation constant of the (III) americium complex and the formation constants of the lanthanide complexes. In addition, light lanthanides ($Nd^{3+}$) and heavy lanthanides ($Er^{3+}$) form complexes of comparable stability.

In the case of the $Nd^{3+}$ complex formed from compound 2, which has two alkyl groups, the constant is much weaker, probably due to a problem of the spherical space requirement of the ligand.

According to the invention, use is preferably made of amides having a single alkyl or alkoxy group for obtaining a satisfactory extraction of the actinides.

EXAMPLES 6 TO 9

In these examples use is made of compound 2 for separating the americium from the europium present in nitric aqueous solution having a nitric acid concentration of 0.01 mole/l and to which is added ammonium thiocyanate.

To this end, contact takes place between one volume of the aqueous solution containing the americium and theeuropium with one volume of an organic solvent constituted by compound 2 diluted in benzene with a concentration of 2 mole/l. Contacting takes place at ambient temperature and accompanied by stirring for 6 minutes, then the two phases are allowed to settle and their respective americium and europium contents are measured by gamma spectrometry.

On the basis of the values obtained, the distribution coefficients $D_{Am}$ of americium and $D_{Eu}$ of europium are determined, i.e. the ratio of the americium or europium concentration in the organic phase to the americium or europium concentration in the aqueous phase. On the basis of these distribution coefficients, a calculation takes place of the americium/europium separation factor FS, which is equal to the ratio $D_{Am}/D_{Eu}$.

The results obtained for ammonium thiocyanate concentrations of the nitric solution between 0.025 and 0.2 mole/l are given in Table 3. These results show that a high separation factor is in particular obtained when the ammonium thiocyanate concentration is 0.1 mole/l.

EXAMPLES 10 TO 13

These examples follow the same operating procedure as in examples 6 and 9, but using as the extractant compound 3 at a concentration of 2 mole/l in benzene. The results obtained are given in Table 3.

These results make it clear that a good americium/europium separation factor is also obtained and that the americium extraction coefficients are higher.

EXAMPLES 14 TO 16

These examples adopt the same operating procedure as in examples 6 to 9 for separating the americium from the europium present in an aqueous solution, but the extractant used is compound 1 at a concentration of 1.78 mole/l in tert. butyl benzene.

The results obtained are given in Table 3. These results make it clear that good americium/europium separation factors are obtained, but the distribution coefficients are lower than in examples 10 to 13.

EXAMPLES 17 TO 19

These examples follow the same operating procedure as in examples 6 to 9 for separating the americium from the europium, but the extractant used is compound 4 in the pure state.

The americium and europium distribution coefficients and the separation factor are given in Table 3. These results make it clear that good separation factors are obtained and there are higher americium extraction coefficients than in the preceding examples.

EXAMPLES 20 AND 21

These examples follow the same operating procedure as in examples 6 to 9, but the extractant used is compound 4 diluted in benzene at a concentration of 2 mole/l.

The results obtained are given in Table 3. These results make it clear that good separation factors are obtained, but the extraction coefficients are lower than in examples 17 to 19.

EXAMPLES 22 TO 25

These examples use compound 3 for separating the americium from the europium on the basis of a nitric acid solution having a nitric acid concentration of 0.01 mole/l, to which has been added lithium nitrate.

Contacting takes place between one volume of the aqueous solution and one volume of the organic solvent, at ambient temperature and accompanied by stirring. After stirring for 6 minutes, the two phases are allowed to settle and their respective americium and europium contents are measured. On the basis of these values, the distribution coefficients $D_{Am}$, $D_{Eu}$ and the separation factor FS are calculated.

The results obtained for $LiNO_3$ concentrations from 5 to 8 mole/l are given in Table 4. These results make it clear that the separation factor is less high than in the case where ammonium thiocyanate is added, but the americium distribution coefficients are high.

EXAMPLES 26 TO 30

The same operating procedure as in examples 22 to 25 is adopted for separating the americium from the europium present in a nitric aqueous solution containing 0.01 mole/l of nitric acid and using pure compound 3 as the extractant.

The results obtained on varying the lithium nitrate concentration of the aqueous solution from 4 to 8 mole/l are given in Table 4.

EXAMPLES 31 TO 36

These examples adopt the same operating procedure as in examples 22 to 25, but the extractant used is compound 1 diluted in tert. butyl benzene at a concentration of 1.78 mole/l.

The results obtained with lithium nitrate concentrations between 4 and 9 mole/l are given in Table 4.

EXAMPLES 37 TO 39

These examples follow the same operating procedure as in examples 22 to 25, but the extractant used is compound 1 diluted in dibutyl formamide at a concentration of 1.72 mole/l.

The results obtained on varying the lithium nitrate concentration of the aqueous solution from 2 to 5 mole/l are given in Table 4.

EXAMPLES 40 TO 42

These examples follow the same operating procedure as in examples 22 to 25, but compound 4 in the pure state is used as the extractant.

The results obtained with lithium nitrate concentrations of 1 to 3 mole/l are given in Table 4.

EXAMPLES 43 TO 46

These examples follow the same operating procedure as in examples 22 to 25, but the extractant is constituted by compound 4 diluted in benzene at a concentration of 2 mole/l.

The results obtained with lithium nitrate concentrations of 5 to 8 mole/l are given in Table 4. The results of the latter show that the separation factors are lower than in the case of thiocyanate solutions, but still make it possible to obtain a good americium/europium separation.

TABLE 1

| Ex | Amide | Starting amine |
|---|---|---|
| 1 | <br>Compound 1<br>m.p. = 47° C. | $C_{12}H_{25}-NH_2$ |
| 2 | <br>Compound 2 |  |
| 3 | <br>Compound 3 | $C_4H_9-NH_2$ |
| 4 | 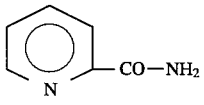<br>Compound 4 | $C_8H_{17}-NH_2$ |

TABLE 2

Formation constants of the complexes of (III) lanthanide ions and (III) americium with various amides.

| Amide | Study medium | $\beta_{11}Nd^{3+}$ | $\beta_{11}Er^{3+}$ | $\beta_{11}Am^{3+}$ |
|---|---|---|---|---|
| 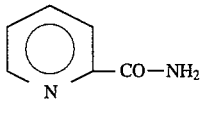 | water – pH 4<br>I = 1.0* | 2.0 | 3.1 | 75 |
| 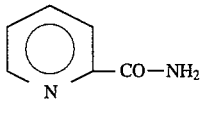 | Methanol + 3% $H_2O$ | 18 | — | — |
| 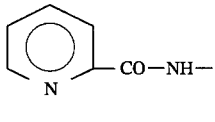<br>(compound 3) | Methanol + 3% $H_2O$ | 8 | — | 54 |
| 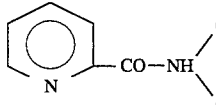<br>(compound 2) | Methanol + 3% $H_2O$ | 0.1 | | |

— Not measured
*Ionic force

TABLE 3
| Organic solvent | Ex. | Aqueous solution | | $D_{Am}$ | $D_{Eu}$ | FS |
| --- | --- | --- | --- | --- | --- | --- |
| | | $HNO_3$ (mole/l) | $NH_4SCN$ (mole/l) | | | |
| Compound 2 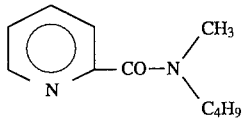 2 mole/l in benzene | 6 | 0.01 | 0.025 | 0.155 | 0.0074 | 20.4 |
| | 7 | 0.01 | 0.05 | 1.33 | 0.053 | 25.2 |
| | 8 | 0.01 | 0.1 | 3.92 | 0.076 | 51.5 |
| | 9 | 0.01 | 0.2 | 7.79 | 0.74 | 10.4 |
| Compound 3 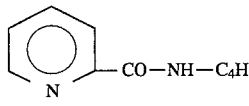 2 mole/l in benzene | 10 | 0.01 | 0.025 | 0.36 | 0.011 | 33.4 |
| | 11 | 0.01 | 0.05 | 1.84 | 0.05 | 36.7 |
| | 12 | 0.01 | 0.1 | 7.68 | 0.256 | 30.0 |
| | 13 | 0.01 | 0.2 | 26.9 | 0.86 | 31.4 |
| Compound 1 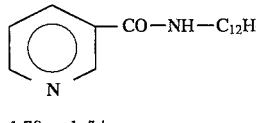 1.78 mole/l in tert. butyl benzene | 14 | 0.01 | 0.1 | 0.309 | 0.0092 | 33.6 |
| | 15 | 0.01 | 0.2 | 1.42 | 0.043 | 33.0 |
| | 16 | 0.01 | 0.3 | 5.01 | 0.15 | 33.2 |
| Compound 4 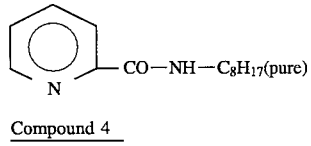 | 17 | 0.01 | 0.025 | 5.34 | 0.17 | 31.4 |
| | 18 | 0.01 | 0.05 | 32 | 1.0 | 32 |
| | 19 | 0.01 | 0.1 | 171 | 7.84 | 21.8 |
| Compound 4 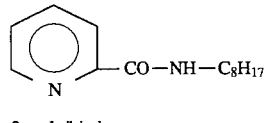 2 mole/l in benzene | 20 | 0.01 | 0.1 | 0.32 | 0.01 | 32 |
| | 21 | 0.01 | 0.25 | 2.91 | 0.09 | 32.2 |
TABLE 4
| Organic solvent | Ex. | Aqueous solution | | $D_{Am}$ | $D_{Eu}$ | FS |
| --- | --- | --- | --- | --- | --- | --- |
| | | $HNO_3$ (mole/l) | $LiNO_3$ (mole/l) | | | |
| Compound 3 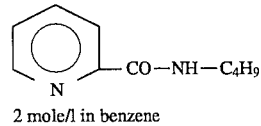 2 mole/l in benzene | 22 | 0.01 | 5 | 1.86 | 0.42 | 4.4 |
| | 23 | 0.01 | 6 | 5.83 | 1.42 | 4.1 |
| | 24 | 0.01 | 7 | 28.3 | 7.75 | 3.6 |
| | 25 | 0.01 | 8 | 107 | 37.7 | 2.8 |
| Compound 3 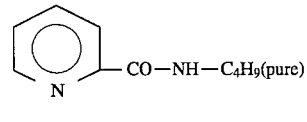 | 26 | 0.01 | 4 | 0.86 | 0.29 | 2.9 |
| | 27 | 0.01 | 5 | 2.53 | 0.94 | 2.7 |
| | 28 | 0.01 | 6 | 6.48 | 2.51 | 2.5 |
| | 29 | 0.01 | 7 | 29.63 | 13.16 | 2.2 |
| | 30 | 0.01 | 8 | 75.6 | 43.9 | 1.7 |

TABLE 4-continued

| Organic solvent | Ex. | Aqueous solution HNO₃ (mole/l) | LiNO₃ (mole/l) | $D_{Am}$ | $D_{Eu}$ | FS |
|---|---|---|---|---|---|---|
| Compound 1 | | | | | | |
| 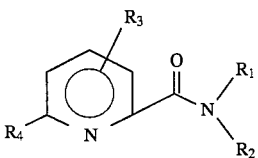 1.78 mole/l in tert. butyl benzene | 31 | 0.01 | 4 | 0.26 | 0.046 | 4.8 |
| | 32 | 0.01 | 5 | 0.74 | 0.16 | 4.5 |
| | 33 | 0.01 | 6 | 2.07 | 0.54 | 3.8 |
| | 34 | 0.01 | 7 | 9.0 | 2.72 | 3.3 |
| | 35 | 0.01 | 8 | 39.85 | 12.57 | 3.2 |
| | 36 | 0.01 | 9 | 80.92 | 30.17 | 2.7 |
| Compound 1 | | | | | | |
| 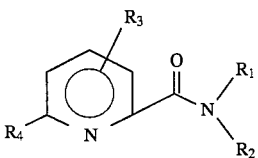 1.72 mole/l in dibutyl formamide | 37 | 0.01 | 2 | 2.45 | 0.86 | 2.8 |
| | 38 | 0.01 | 3 | 13.18 | 4.92 | 2.7 |
| | 39 | 0.01 | 5 | 172.0 | 71.96 | 2.4 |
| Compound 4 | | | | | | |
| 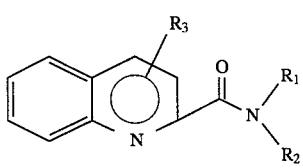 | 40 | 0.01 | 1 | 0.84 | 0.097 | 8.6 |
| | 41 | 0.01 | 2 | 5.68 | 0.71 | 7.9 |
| | 42 | 0.01 | 3 | 29.8 | 3.8 | 7.7 |
| Compound 4 | | | | | | |
| 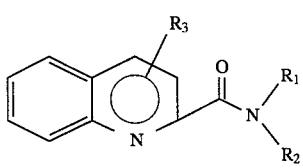 2 mole/l in benzene | 43 | 0.01 | 5 | 3.22 | 0.70 | 4.6 |
| | 44 | 0.01 | 6 | 11.0 | 2.69 | 4.1 |
| | 45 | 0.01 | 7 | 19.3 | 5.01 | 3.8 |
| | 46 | 0.01 | 8 | 98.4 | 32.6 | 3.0 |

We claim:

1. Process for the selective extraction of trivalent actinides present in aqueous solution, wherein said aqueous solution contains nitric acid at a concentration below about 0.5 mole/l and also contains lanthanides, said process comprising: contacting the aqueous solution with an organic solution containing an amide having a nitrogenous heterocyclic substituent of formula:

$$\text{(I)}$$

$$\text{or}$$

$$\text{(II)}$$

in which $R_1$, $R_2$, and $R_3$, which are the same or different, represent a hydrogen atom, or an alkyl or alkoxy group, and, $R_4$ represents a hydrogen atom or a group of formula:

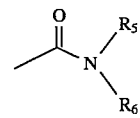

in which $R_5$ and $R_6$, which are the same or different, represent a hydrogen atom, or an alkyl or alkoxy group, to extract the actinides and form an organic phase containing the extracted actinides and an aqueous phase from which the actinides have been extracted; and separating the organic phase from the aqueous phase.

2. Process according to claim 1, wherein $R_1$ represents an alkyl or alkoxy group and $R_2$ represents a hydrogen atom.

3. Process according to claim 1 wherein the amide is in accordance with formula (I) with $R_1$ representing an alkyl group and $R_2$, $R_3$, and $R_4$ representing a hydrogen atom.

4. Process according to claim 3, wherein the alkyl group is selected from the group consisting of butyl, octyl and dodecyl alkyl group.

5. Process according to claim 1, wherein the organic solution comprises an organic diluent.

6. Process according to claim 5, characterized in that the organic diluent is selected from the group consisting of benzene, benzene derivatives and dimethyl formamide.

7. Process according to claim 1, wherein a compound chosen from among nitrates and thiocyanates is added to the aqueous solution containing nitric acid to thereby obtain a concentration of said compound in the aqueous solution.

8. Process according to claim 7, wherein the concentration of thiocyanate in the aqueous solution containing nitric acid is in the range of about 0.025 to 2 mole/l.

9. Process according to claim 7, wherein the aqueous solution containing nitric acid is further comprised of sodium or lithium nitrate in a concentration range of about 1 to 10 mole/l.

10. Process for the selective extraction of trivalent actinides present in an aqueous solution, wherein said aqueous solution contains nitric acid at a concentration below about 0.5 mole/l comprising:

a) contacting said aqueous solution with an organic solution incorporating at least one amide having a nitrogenous heterocyclic substituent of formula:

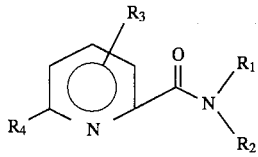

(I)

or

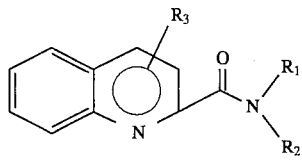

(II)

in which $R_1$ is a hydrogen atom, or an alkyl or alkoxy group, $R_2$ and $R_3$, which are the same or different, represent a hydrogen atom, or an alkyl or alkoxy group; and, $R_4$ represents a hydrogen atom or a group of formula:

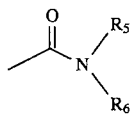

in which $R_5$ and $R_6$, which are the same or different, represent a hydrogen atom, or an alkyl or alkoxy group, to extract the actinides and form an organic phase containing the extracted actinides and an aqueous phase from which the actinides have been extracted; and b) separating the organic phase from the aqueous phase.

11. Process according to claim 10, wherein a compound chosen from among nitrates and thiocyanates is added to the aqueous solution containing nitric acid to thereby obtain a concentration of said compound in said aqueous solution.

12. Process according to claim 11, wherein the concentration of thiocyanate in the aqueous solution containing nitric acid is in the range of about 0.025 to 2 mole/l.

13. Process according to claim 10, wherein the aqueous solution is further comprised of sodium or lithium nitrate in a concentration range of about 1 to 10 mole/l.

14. Process according to claim 11, wherein the aqueous solution is further comprised of sodium or lithium nitrate in a concentration range of about 1 to 10 mole/l.

15. Process according to claim 10, wherein the organic solution comprises an organic diluent.

16. Process according to claim 15, wherein the organic diluent is selected from the group consisting of benzene, benzene derivatives, and dimethyl formamide.

* * * * *